(12) United States Patent
Whalen et al.

(10) Patent No.: US 6,395,314 B1
(45) Date of Patent: *May 28, 2002

(54) PROCESS FOR FORMING AN OAT-BASED FROZEN CONFECTION

(75) Inventors: Paul J. Whalen, Elk River; Donald L. Maxwell, Plymouth; Donald Wilbur, Minnetonka, all of MN (US)

(73) Assignee: American Oats, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 09/414,216

(22) Filed: Oct. 7, 1999

Related U.S. Application Data

(60) Division of application No. 09/033,375, filed on Mar. 2, 1998, now Pat. No. 5,989,598, which is a continuation-in-part of application No. 08/591,863, filed on Jan. 25, 1996, now Pat. No. 5,723,162, which is a continuation-in-part of application No. 08/379,398, filed on Jan. 26, 1995, now abandoned.

(51) Int. Cl.[7] ............................................. A23B 1/105
(52) U.S. Cl. ........................... 426/28; 426/20; 426/100; 426/549; 426/565
(58) Field of Search ............................ 426/28, 20, 100, 426/549, 565

(56) References Cited

U.S. PATENT DOCUMENTS

| | | | |
|---|---|---|---|
| 3,644,126 A | 2/1972 | Bodnar et al. ............... 99/142 |
| 4,199,605 A | 4/1980 | Kahn et al. ............... 426/330.6 |
| 4,244,981 A | 1/1981 | Blake ........................ 426/567 |
| 4,311,714 A | 1/1982 | Goering et al. ............... 426/28 |
| 4,335,155 A | 6/1982 | Blake et al. ............... 426/565 |
| 4,374,890 A | 2/1983 | Gasser et al. ............... 426/28 |
| 4,428,967 A | 1/1984 | Goering et al. ............... 426/28 |
| 4,510,166 A | 4/1985 | Lenchin et al. ............. 426/565 |
| 4,744,992 A | 5/1988 | Mitchell et al. ............. 426/29 |
| 4,804,545 A | 2/1989 | Goering et al. ............... 426/28 |
| 4,871,571 A | 10/1989 | Jensen et al. ............... 426/548 |
| 4,894,242 A | 1/1990 | Mitchell et al. ............. 426/29 |
| 4,908,223 A | 3/1990 | Murtaugh .................. 426/565 |
| 4,948,614 A | 8/1990 | Feldpausch ................ 426/565 |
| 4,954,360 A | 9/1990 | Barnett ..................... 426/565 |
| 4,990,344 A | 2/1991 | Euber et al. ................ 426/28 |
| 4,996,063 A | 2/1991 | Inglett ....................... 426/21 |
| 5,013,561 A | 5/1991 | Goering et al. ............... 426/28 |
| 5,082,673 A | 1/1992 | Inglett ....................... 426/21 |
| 5,110,612 A | 5/1992 | Quarles et al. ............. 426/548 |
| 5,234,704 A | 8/1993 | Devine et al. ............. 426/565 |
| RE34,508 E | 1/1994 | Murtaugh et al. .......... 426/565 |
| 5,393,550 A | 2/1995 | Tarr et al. .................. 426/573 |
| 5,407,694 A | 4/1995 | Devine et al. ............. 426/565 |
| 5,723,162 A * | 3/1998 | Whalen et al. ............... 426/28 |
| 5,989,598 A * | 11/1999 | Whalen et al. ............... 426/28 |

FOREIGN PATENT DOCUMENTS

| | | | |
|---|---|---|---|
| EP | 0 031 050 | * | 11/1980 |
| EP | 0 487 187 A1 | | 8/1991 |
| EP | 0 486 936 A1 | | 11/1991 |
| EP | 0 540 421 A1 | | 10/1992 |
| WO | 95/07628 | | 3/1995 |
| WO | 95/10196 | | 4/1995 |

OTHER PUBLICATIONS

Janet Raloff, Beyond OAt Bran–Reaping the benefits without gorging on the grain, beginning on p. 62 (3 pages) of Food Technology.

Elizabeth Bertini, Make Room for Oat Milk, p. 72 of National Foods Merchandise.

Novo Industi A/S Enzymes Division, Novo's Handbook of Practical Biotechnology, 1986 pp. 35–41.

* cited by examiner

*Primary Examiner*—Helen Pratt
(74) *Attorney, Agent, or Firm*—Patterson, Thuente, Skaar & Christensen, P.A.

(57) ABSTRACT

A process for forming a syrup product that is suitable for use as a non-dairy frozen confection. The non-dairy frozen confection exhibits selected sweetness, texture, and mouthfeel characteristics while being devoid of exogenous sweeteners, stabilizers, emulsifiers, and proteins. The process includes blending a base formulation and water to form a slurry, the base formulation having a major amount of an oat material or waxy barley hybrid flour. The process also includes liquefying and saccharifying the slurry to produce the syrup product.

5 Claims, No Drawings

PROCESS FOR FORMING AN OAT-BASED FROZEN CONFECTION

RELATED U.S. APPLICATION DATA

This application is a Divisional application of Ser. No. 09/033,375, filed Mar. 2, 1998, which is now U.S. Pat. No. 5,989,598, which is a Continuation-in-Part application of Ser. No. 08/591,863, filed Jan. 25, 1996, now U.S. Pat. No. 5,723,162, which is a Continuation-in-Part application of Ser. No. 08/379,398, filed Jan. 26, 1995, now abandoned.

BACKGROUND OF THE INVENTION

The present invention relates generally to frozen confections and beverages. More particularly, the present invention relates to a process for forming an oat-based, non-dairy frozen confection and an oat-based, non-dairy beverage.

Consumers are increasingly concerned about purchasing and consuming products that the consumers view as being more healthful. For example, products possessing higher levels of complex carbohydrates and fiber, especially soluble fiber, are becoming more popular with consumers. In addition, products containing lower levels of fat and cholesterol as well as a decreased caloric content are becoming more popular with consumers. Many consumers also desire products made from all-natural components that contain no stabilizers, emulsifiers, or other exogenous additives, such as refined sugars or artificial sweeteners.

Non-dairy sweet confections are becoming popular alternatives to conventional dairy-based frozen confections. Consumers who are lactose intolerant are especially interested in purchasing products that do not contain dairy products or dairy derivatives.

One drawback of products produced for the health conscious market is that they tend to be less sweet than conventional dairy-based frozen desserts. This problem has been overcome by the addition of various sweeteners, such as sucrose, glucose syrup, and high fructose corn syrup. While these products may appeal to some segments of the health conscious market, these products are not desired by consumers who exclude refined or artificial sweeteners from their diet.

A variety of non-dairy compositions have been developed that appeal to the various segments of the health conscious market. Unfortunately, none of the products deliver all of the benefits of being lactose free, high in soluble fiber, free of exogenous additives, and sweet without the addition of refined sugars and artificial sweeteners. A product that delivers all these benefits would be acceptable as a substitute for dairy-based products even by consumers who are not interested in the health benefits of such a product.

An article by Janet Raloff (Beyond Oat Bran, Food Technology 1991 (8), at 62) describes the physiological benefits of consuming an oat-based product, which is identified by the name Oatrim. The oat-based product is formulated from either oat bran or oat flour. The article indicates that the odorless and nearly tasteless oat-based product is particularly suited as a fat replacement in low-temperature applications, such as frozen confections.

The oat-based product is described in further detail in Inglett, U.S. Pat. Nos. 4,996,063 and 5,082,673. A mixture of oats and water is gelatinized by passage through a steam injection cooker at a temperature of between 138° C. and 143° C. After the pH of the mixture is adjusted, alpha-amylase enzymes are added to hydrolyze the starch in the mixture. Once hydrolyzation is complete, soluble fiber is separated from the mixture. Finally, the soluble fiber is dehydrated to provide the oat-based product. Examples in the Inglett patents indicate that the oat-based product is mixed with additional components, such as milk and sugar, to formulate the frozen confection.

Mitchell et al., U.S. Pat. No. 4,744,992, discloses using a dual enzyme method, which includes liquefying and saccharifying rice, to produce a high glucose syrup. Examples in the Mitchell et al. patent indicate that when the syrup is incorporated into a frozen confection, vegetable oil in a concentration of approximately 10 percent by weight of the frozen confection as well as stabilizers are added to provide the frozen confection with a creamy texture.

Murtaugh et al., U.S. Pat. No 4,908,223, discloses an oat- or rice-based frozen confection and a method of preparing the frozen confection. Murtaugh et al. describes cooking an aqueous mixture of oats or rice. After the cooking is complete, liquefying, sweetening, and flavoring agents are added to the mixture so that the frozen confection exhibits ice cream-like characteristics.

Murtaugh et al., U.S. Pat. No. 4,908,223, discloses an oat or rice-based frozen confection and a method of preparation. Murtaugh et al. describes that refined sweeteners are added to improve the functional and organoleptic properties of the product.

Several fruit-based frozen confections have also been developed. For example, Feldpausch, U.S. Pat. No. 4,948,614, describes using bananas to produce a non-dairy confection. Blake et al., U.S. Pat. No. 4,335,155, discloses that any fruit, which can be made into a puree, is suitable for use as a base of a frozen confection. Blake, U.S. Pat. No. 4,244,981, describes using citrus juice vesicles as the primary component of a frozen confection.

SUMMARY OF THE INVENTION

The present invention includes a process for forming a non-dairy frozen confection. The non-dairy frozen confection is formed from a syrup that is frozen using conventional techniques. The syrup product is produced by liquefying and saccharifying a starch source, which is primarily oat flour or waxy barley hybrid flour. The non-dairy frozen confection exhibits ice cream-like characteristics without exogenous sweeteners, stabilizers, emulsifiers, or proteins.

DETAILED DESCRIPTION OF THE PREFERRED EMBODIMENTS

The present invention includes a process for forming a non-dairy, frozen confection. The frozen confection is made from a sweet, bland, and clean tasting syrup product. The syrup product is substantially prepared from oat flour or waxy barley hybrid flour.

The frozen confection of the present invention has several advantages over prior art frozen confections. The frozen confection exhibits desirable sweetness, texture, and mouthfeel characteristics without exogenous sweeteners, stabilizers, emulsifiers, or proteins, which are commonly used in prior art non-dairy frozen confections. As used herein, the term "mouthfeel" refers to a creamy sensation that a person experiences in one's mouth upon consuming ice cream. As used herein, the term "exogenous" refers to components that are added to prior art frozen confections to supplement or modify the characteristics of the prior art frozen confections.

Furthermore, when producing the frozen confection of the present invention, the syrup product does not require emulsification or homogenization. The prior art non-dairy frozen confections typically require emulsification and homogenization to produce characteristics that are commonly associated with dairy-based frozen confections.

The properties of the frozen confection are dictated by the particular oat or grain components selected. It has been found that using a low bran flour, which is depleted in bran while retaining soluble fiber glucans, provides a frozen confection with desired characteristics. The typical compositional analysis of low bran oat flour is similar to whole oat flour for moisture, protein, and fat, as illustrated in Table 1. However, low bran oat flour contains a lower level of bran than whole oat flour. Low bran oat flour also retains a substantial percentage of the soluble fiber that is present in whole oat flour.

TABLE 1

| Composition (weight percent) | Whole Oat Flour | Low Bran Oat Flour | Patent Oat Flour |
| --- | --- | --- | --- |
| Moisture | 11 | 11 | 10 |
| Protein | 18 | 15 | 11 |
| Fat | 7 | 7 | 5–6 |
| Total Dietary Fiber | 9 | 10 | 3–4 |
| Beta-Glucan | 4 | 7 | 1–2 |

While it is also possible to use oats or grains having a significant hull, bran, or husk portion to formulate the syrup, syrup formed from these materials must be separated from insoluble branny particles present in the syrup before the frozen confection is produced from the syrup. As an alternative to using the oats in the form of flour, it is also possible to practice the present invention with other forms of oats, such as rolled oats, partially milled oats, and oatmeal. These various forms of oats are collectively identified as "oat material".

One particular oat flour possessing a low level of bran or hull material is patent oat flour. Patent oat flour is a fraction of the whole oat flour obtained from a mill stream early in the oat milling process. The patent oat flour contains a smaller concentration of the bran or hull material than oat flour stream occurring later or downstream in the milling process. This oat flour is referred to as patent oat flour because it has similar characteristics to patent wheat flour that is produced by a process commonly used in the production of wheat flour for bread or other baked products.

The typical compositional analysis of patent oat flour is similar to whole oat flour for moisture, protein, and fat, as illustrated in Table 1. Patent oat flour also retains a substantial percentage of the soluble fiber that is present in whole oat flour. However, patent oat flour contains less bran or insoluble fiber and more starch than whole oat flour.

The various fractions formed in the oat milling stream produce frozen products with varied characteristics. The fractions high in soluble fiber, including whole oat flour and oatmeal tend to give very smooth and somewhat "dry" texture to soft-serve frozen dessert, while those higher in starch content (e.g., patent oat flour) tend to provide more sweetness. It will be obvious to those skilled in the art that a desired set of finished product characteristics may be obtained by selecting an appropriate oat starting material or blend of available oat milling fractions. For example, the frozen confection may be formed from a mixture of patent oat flour and whole oat flour. Oat mill products possessing these characteristics can be obtained from various sources including Conagra, Inc (Council Bluffs, Iowa) or Grain Millers (Minneapolis, Minn.).

It has also been found that a waxy barley hybrid flour also provides desirable results when used with the present invention. The waxy barley hybrid is a hull-less barley that is preferably selected from the prowashneupana variety, which can be obtained from Conagra, Inc. (Council Bluff, Iowa). The typical compositional analysis for the prowashneupana waxy barley hybrid is set forth in Table 2.

TABLE 2

| Composition (weight percent) | Waxy Barley Hybrid Flour |
| --- | --- |
| Moisture | 14 |
| Protein | 20 |
| Fat | 7 |
| Total Dietary Fiber | 29 |
| Beta-Glucan | 14 |

Other starch sources can be used in conjunction with the oat flour or waxy barley hybrid flour to adjust the flavor and sweetness of the frozen confection. While other starch sources may be used in the preparation of the frozen confection, the other starch sources only represent a minor portion of oat or grain material that is used to prepare the frozen confection. The oat flour and waxy barley hybrid flour comprise a major portion of the oat or grain material that is used to prepare the frozen confection.

Examples of starch sources that are suitable for use in the present invention include flours, such as corn flour, wheat flour, rice flour, and potato flour. It is believed that the addition of other starch sources to the oat flour or waxy barley hybrid flour does not affect the functional properties of the frozen confection, such as texture and mouthfeel characteristics, associated with ice cream-like qualities.

As a preliminary step in the preparation of the frozen confection, the oat flour or waxy barley hybrid flour may be milled to a fine granulation. The term "fine granulation" means less than 10 percent of the oat flour or waxy barley hybrid flour was retained on a 200 U.S. mesh screen.

A base formulation is created by blending the selected starch sources. A slurry is formed by mixing the base formulation into water in an amount that is effective to provide a solids level of between 25 and 33 percent on a dry matter basis. The water is preferably potable tap water that is provided at a traditional faucet temperature of about 10° C.

Changing the solids level allows the sweetness of the non-dairy frozen confection to be adjusted. For example, increasing the solids level causes an increase in the sweetness of the non-dairy frozen confection.

Alpha-amylase enzymes are then added to the slurry. The alpha-amylase enzymes are preferably alpha-1,4-glucan, 4-glucanohydrolase, which is derived from *Bacillus subtilis*. The alpha-amylase enzymes not only produce liquefaction in a random fashion over a broad range of temperatures (65° C. to 92° C.) but also retain its activity when used at temperatures of less than 80° C.

The alpha-amylase enzymes are preferably food grade alpha-amylase enzymes, which can be obtained from Genencor International (Rochester, N.Y.) under the designation MULTIFECT H-39C. The MULTIFECT H-39C enzymes are added to the slurry in a concentration of between 0.0020 and 0.0080 percent by weight of the slurry and preferably in a concentration of approximately 0.0040 percent by weight of the slurry.

Converting the starch mixture into the syrup product is preferably accomplished using a three-step process. The first step, which is referred to as liquefaction, involves converting the slurry into an intermediate syrup. Liquefaction includes two elements. In the first element, microscopic starch granules in the starch mixture swell and eventually rupture. Rupturing of the microscopic starch granules causes the viscosity of the slurry to significantly increase. Once the viscosity of the slurry significantly increases, the starch is referred to as being gelatinized. Gelatinization renders the starch more susceptible to partial hydrolysis.

In the second element, the alpha-amylase enzymes cause the starch to partially hydrolyze into dextrin. In conjunction with the partial hydrolysis of the starch, the viscosity of the slurry is reduced.

The slurry is heated to a temperature of approximately 58° C. to 60° C. at which the viscosity of the slurry visibly increases. As an alternative to visually observing the increase in the slurry viscosity, the viscosity increase in the slurry may be determined by monitoring the amperage requirement of the mixing motor.

After the viscosity of the slurry increases, the rate at which the slurry is heated is decreased to allow the slurry to uniformly gel. The decreased heating rate also avoids scorching the slurry, which results from the rapid decrease in heat transfer caused by the increase in the viscosity of the slurry. Once the slurry reaches a target temperature of approximately 75° C., the slurry is maintained at the target temperature for approximately 1 hour.

The hold time allows the alpha-amylase enzymes to liquify the starch as the starch gels by converting the starch into dextrin. The conversion of starch into dextrin causes the slurry to change into an intermediate syrup. As the slurry is converted into the intermediate syrup, the raw flavor of the slurry is reduced. The reduction of off-flavors in the intermediate syrup can be monitored by tasting samples of the intermediate syrup at selected intervals while the slurry is held at the target temperature.

The intermediate syrup is then hot filtered to remove portions of the slurry that have not been broken down during the liquefaction process. Conventional screens or filters having a U.S. mesh size of 30 or smaller are suitable for use with the present invention. The filtered intermediate syrup is then cooled to a saccharification temperature of between approximately 60° C. and 65° C.

In the second step, which is referred to as saccharification, the dextrin in the filtered intermediate syrup is converted into glucose. The conversion of dextrin into glucose causes the syrup product to exhibit a high degree of sweetness.

The dextrin is preferably converted into glucose using glucoamylase enzymes. The glucoamylase enzymes are also referred to as fungal 1,4-alpha-D-glucan glucohydrolase, which can be obtained from Genencor International (Rochester, N.Y.) under the designation SPEZYME GA 300.

The concentration of the glucoamylase enzymes is selected based upon the desired length of the saccharification time. For example, it has been found that using a glucoamylase enzyme concentration of between 0.090 and 0.130 percent by weight of the filtered intermediate syrup provides a saccharification time of between 1 and 3 hours. Alternatively, using a glucoamylase enzyme concentration of approximately 0.016 percent by weight of the filtered intermediate syrup with a saccharification time of up to 24 hours provides a syrup product with similar properties.

An advantage of using glucoamylase enzymes in the process of the present invention is that the pH of the filtered intermediate syrup does not have to be adjusted to obtain a desired enzyme activity.

At a given concentration of glucoamylase enzymes, the sweetness of the syrup product can be changed by varying the saccharification time. For example, increasing the saccharification time increases the sweetness of the syrup product. While it is possible to obtain higher sweetness levels by increasing the glucoamylase concentration with a commercially reasonable saccharification time of less than 3 hours, the higher concentration may adversely affect the flavor of the finished syrup product. Using longer saccharification times of up to 24 hours produce higher sweetness levels but saccharification times in this range may not be commercially feasible.

It has been found that the sweetness of the syrup product can be further enhanced through the use of a third enzyme process that causes the formation of fructose. This conversion is preferably accomplished using an immobilized glucose isomerase enzyme. Immobilized glucose isomerase refers to a preparation of microbially derived glucose isomerase enzyme absorbed on and within a granular and water-insoluble carrier such as silica gel or aluminum oxide. The particle size of the water-insoluble carrier is preferably approximately 30×50 US Standard mesh.

A typically preferred method of treating glucose syrup with immobilized glucose isomerase enzyme is by percolating the glucose syrup through a column or packed bed of immobilized glucose isomerase enzyme. However, the syrup product of the present invention contains significant levels of glucans, hemicelluloses, proteins, and lipids that tend to foul the column or packed bed. Because the glucans, hemicelluloses, proteins, and lipids play a important role in use of the syrup product as a non-dairy frozen confection, it is not possible to remove these components from the syrup product.

To overcome these limitations, the immobilized glucose isomerase enzyme is dispersed in the bulk phase of the syrup product. Introduction of the immobilized glucose isomerase enzyme into the syrup product is done after the initiation of the saccharification step. Preferably, the immobilized glucose isomerase enzyme is introduced into the intermediate syrup immediately following the addition of the saccharifying enzyme. This allows the saccharification of dextrins to form glucose and the subsequent conversion of part of the glucose to occur in the same time frame and at the same temperature. In this procedure, the intermediate syrup is preferably maintained at a temperature of between about 60° C. and 65° C. for between 3 and 4 hours.

A suitable proprietary immobilized glucose isomerase enzyme for use with the present invention is commercially available from UOP (Des Plaines, Ill.) under the name of KETOMAX® GI-101. Another suitable immobilized glucose isomerase enzyme for use in the present invention is available under the designation SWEETZYME® T from Novo Nordisk Biochem (Franklinton, N.C.)

The amount of the immobilized glucose isomerase enzyme used is selected upon the desired amount of additional sweetness in the syrup product. The concentration of the immobilized glucose isomerase enzyme is only limited by the practical rheological properties of the resultant mixture. High loads of enzyme carrier create difficulties with agitation of the mixture and lead to disintegration of the carrier due to abrasion between carrier particles. For most applications, the concentration of immobilized glucose isomerase enzyme is less than 20 percent by volume of the syrup. Preferably, the concentration of immobilized glucose isomerase enzyme is between about 0.5 and 2.0 percent by volume of the syrup.

Following the immobilized glucose isomerase treatment, the immobilized glucose isomerase enzyme is removed by screening. The mesh size of the screen is selected to effectively remove all of the immobilized glucose isomerase enzyme carrier. Selection of a separation method is based on minimizing damage to the glucose isomerase carrier. Methods that cause impact or abrasion damage to the carrier are less desirable due to contamination of the syrup product with fine particles of the carrier material.

A person of ordinary skill in the art will appreciate the various separation techniques, such as basket centrifuge, profile wire screens, filter presses, pressure strainers, and sedimentation vessels. A preferred method of removing the immobilize glucose isomerase enzyme from the syrup product is through a 120 mesh vibratory sifter.

After separation of the immobilized glucose isomerase carrier from the syrup product, the immobilized glucose isomerase enzyme may be reused with subsequent batches of syrup. Alternatively, the immobilized glucose isomerase enzyme is washed with potable water and stored for future use. To protect the enzyme carrier from bacterial deterioration during storage, a preservative is preferably applied to the enzyme carrier prior to storage.

Over time the glucose isomerase enzyme becomes denatured. The extent of enzyme degradation may be determined by tracking the rate of fructose conversion over several lots of syrup. When required, replacement material may be purchased as a single use material, or the exhausted carrier may be regenerated with fresh glucose isomerase enzyme, in a manner familiar to those skilled in the art.

After the syrup product obtains a desired degree of sweetness, the syrup product is cooled to a temperature of approximately 10° C. The syrup product is clean and bland with no off-flavors.

The syrup product may be then flavored as desired using flavoring ingredients that are known in the art. For example, vanilla or cocoa may be added to the syrup product to produce vanilla or chocolate flavored non-dairy frozen confection. It may also be desirable to add a dairy- or cream-like flavor to the syrup product so that the non-dairy frozen confection tastes more similar to ice cream.

The flavor of the syrup product may be enhanced by the addition of a small concentration of a flavor enhancer. Various flavor enhancers are known in the art and are selected based upon the particular flavoring ingredients that are used in the non-dairy frozen confection. It is also possible to enhance the flavor of the non-dairy frozen confection by adding salt in a concentration of approximately 0.35 percent by weight of the syrup product. It is believed that adding salt to the syrup product after the syrup product is formed minimizes off-flavors resulting from the addition of the salt while the syrup product is being prepared.

After the syrup product is flavored, the syrup product is frozen to produce the non-dairy frozen confection. The freezing is accomplished using processes and machines that are conventionally used to produce soft-serve or hard-pack prior art frozen confections.

The non-dairy frozen confection of the present invention surprisingly exhibits desirable functional characteristics of a frozen confection but does not require the use of exogenous sweeteners, stabilizers, emulsifiers, or proteins to produce the desirable functional characteristics. For example, the sweetness of the non-dairy frozen confection results from the glucose and fructose produced during the saccharification and glucose isomerization steps.

The non-dairy frozen confection exhibits desirable viscosity characteristics without the addition of exogenous sweeteners, stabilizers, emulsifiers, or proteins. It is believed that the desirable viscosity characteristics result from the naturally occurring fiber and gums in the starch sources. In particular, the texture of the non-dairy frozen confection depends upon beta-glucan being naturally present at a level sufficient for beta-glucan to act both as a stabilizer and texturizing agent in the syrup product.

Additionally, the non-dairy frozen confection exhibits texture and mouthfeel that are similar to ice cream, frozen yogurt, and other similar frozen confections. It is believed that the naturally occurring fat, protein, and fiber in oats result in the non-dairy frozen confection exhibiting a smooth mouthfeel characteristic. Furthermore, the syrup product does not require emulsification or homogenization to produce the smooth mouthfeel characteristic in the non-dairy frozen confection of the present invention.

A person of ordinary skill in the art would appreciate that additives, such as pectin, gums, emulsifiers such as mono- and di-glycerides, bodying agents including cyclodextrose and maltodextrins, and the like, may be added to change the texture of frozen confections made primarily from oats. However, such additives are unnecessary for the production of a satisfactory soft-serve frozen confection, and would tend to lessen the consumer appeal of a product free of additives.

A person of ordinary skill in the art would also appreciate that the syrup product produced in the present invention could be used to formulate items other than frozen confections. For example, the syrup product may be used to produce shakes, malts, and puddings. The syrup product may also be incorporated into carbohydrate-loading beverages that take advantage of the same physical and nutritional characteristics that make the syrup product of the present invention useful for frozen confections.

The product and method of the present invention are described in the following examples. These examples are provided as an illustration of the invention and are not intended to limit the invention.

EXAMPLE 1

The characteristics of the non-dairy frozen confection of the present invention were studied using a blend of 70 percent by weight patent oat flour and 30 percent by weight rice flour.

A starch mixture was prepared by dry-blending 1.91 kilograms of patent oat flour with 0.82 kilograms of rice flour. Both the patent oat flour and the rice flour had a sufficiently fine granulation such that less than 10 percent of the starch mixture was retained on a 200 U.S. mesh screen.

The starch mixture was then mixed into 6.35 kilograms of potable tap water to form a slurry. Next, 0.36 grams of alpha-amylase enzymes (MULTIFECT H-39C) were added to the slurry.

As the slurry was being mixed, the slurry was heated to a temperature of between approximately 58° C. and 60° C. At this point, the viscosity of the slurry noticeably increased. The rate of heating was then decreased to avoid scorching the slurry. Once the slurry reached a target temperature of approximately 75° C., the slurry was maintained at the target temperature for 1 hour to allow the slurry to be converted into an intermediate syrup.

Next, the intermediate syrup was hot filtered through a 30 U.S. mesh screen to remove unconverted portions of the slurry. The filtered intermediate syrup was then cooled to approximately 60° C.

While mixing, 8.6 grams of glucoamylase enzymes (SPEZYME GA 300) was added to the filtered intermediate syrup. The mixing was continued while the filtered intermediate syrup was maintained at approximately 60° C. for 3 hours such that the syrup product was formed.

The syrup product was then cooled to approximately 10° C. and 6.63 grams of salt were mixed into the syrup product. The syrup product was sweet, bland, and clean-tasting.

EXAMPLE 2

In a continuously stirred vessel approximately 6 pounds of low bran oat flour were mixed with approximately 14 pounds of water and about 0.36 grams of alpha-amylase to form a slurry. The slurry was heated to approximately 62° C. in 14 minutes. The slurry was then further heated to about 75° C. in an additional 10 minutes and held at 75° C. for one hour to convert the slurry into an intermediate syrup. Next, the intermediate syrup was cooled to approximately 60° C. in 11 minutes, and about 8.6 grams of glucoamylase added. The intermediate syrup was maintained at a temperature of 60° C. for approximately 105 minutes to convert the intermediate syrup into a syrup.

The syrup was chilled and filtered through a 40 mesh screen. Next, the syrup was then filtered through a conical filter with a slotted medium having slots about 200 microns wide. The sugar content of the filtered syrup was examined using a Brix analysis and found to have a refractive index corresponding to a 21 percent by weight sugar content.

A mixture was formed by combining the filtered syrup with flavoring agents at a concentration of approximately 2 percent by weight, cocoa at a concentration of approximately 2 percent, and salt at a concentration of approximately 0.2 percent. Finally, the mixture was frozen in a soft-serve machine (Taylor Model 152) to produce a frozen confection. The frozen confection was sampled and determined to have desirable texture characteristics.

EXAMPLE 3

In a continuously stirred vessel, approximately 6 pounds of low bran oat flour were mixed with approximately 14 pounds mineral water and about 0.36 grams of alpha-amylase to form a slurry. The slurry was heated to approximately 60° C. in 18 minutes. The slurry was then further heated to about 75° C. in an additional 13 minutes and held at 75° C. for 65 minutes to convert the slurry into an intermediate syrup. The intermediate syrup was then cooled to approximately 59° C. in 11 minutes, and about 8.6 grams of glucoamylase was added. The intermediate syrup was maintained at approximately 59° C. to convert the intermediate syrup to a syrup.

The syrup was first cooled and then filtered with a conical filter having slots approximately 200 microns wide, by continuous agitation. Filtering separated a wet bran cake weighing approximately 475 grams from the filtered syrup, which weighed approximately 3000 grams. A mixture was then formed by blending the filtered syrup with flavoring agents at a concentration of approximately 2 percent by weight, cocoa at a concentration of approximately 2 percent by weight, and salt at a concentration of approximately 0.2 percent by weight. After the mixture was frozen in a soft-serve machine to produce a frozen confection, the frozen confection was found to have a desirable texture. The frozen confection was stored in a household type refrigerator for 17 days and found to have a texture similar to commercial low-fat frozen desserts after this time period.

EXAMPLE 4

A slurry was formed by dispersing approximately 560 grams of rolled oats and about 0.6 grams of alpha amylase in approximately 1300 grams of cold water. The slurry was held at room temperature for approximately 3 hours. The slurry was then heated to approximately 180° C. over a period of three hours using a hot water bath to convert the slurry into an intermediate syrup. The intermediate syrup was next cooled to approximately 60° C. and mixed with glucoamylase. The intermediate syrup was maintained at about 60° C. for approximately one hour to convert the intermediate syrup into a syrup. After cooling to room temperature, the syrup was filtered through a conical filter with 200 micron slots. When the filtered syrup was flavored and frozen to form a frozen confection, the frozen confection had a smooth and dry texture.

EXAMPLE 5

Cold water (175 pounds), salt (0.5 pounds), alpha amylase (25 grams), and oatmeal (75 pounds) were mixed to form a slurry in a stirred jacketed vessel. The slurry was slowly heated to a temperature of approximately 76° C. over a period of approximately 7 hours to convert the slurry into an intermediate syrup. The intermediate syrup was then cooled to approximately 66° C. Next, glucoamylase was added to the intermediate syrup and the intermediate syrup was held at a temperature of at least approximately 60° C. for approximately 1.5 hours to convert the intermediate syrup into a syrup. The syrup contained an unreacted starch portion that was separated from the syrup by heating the syrup in a simmering water bath for one hour and then filtering through a 200-micron filter. The filtered syrup was flavored and frozen using a soft-serve machine to form a frozen confection that exhibited a very creamy-type texture.

EXAMPLE 6

In a jacketed vessel equipped with wall-wiping agitators, approximately 75 pounds of whole oat flour and about 25 milliliters of alpha-amylase enzyme were mixed into approximately 175 pounds of water to form a slurry. The slurry was heated to a temperature of approximately 58° C. over a period of one hour, and thinned slightly with about 30 pounds of water. The slurry was heated further to 83° C. over approximately one hour to convert the slurry into an intermediate syrup. After cooling to approximately 64° C., the intermediate syrup was mixed with 75 milliliters of glucoamylase. Next, the intermediate syrup was held at a temperature of approximately 60° C. for one hour to convert the intermediate syrup into a syrup. The syrup was then cooled to room temperature and filtered with a juice extraction machine to separate the insoluble fiber from the syrup. The filtered syrup was flavored and frozen in a soft-serve machine (Taylor Model 152) to produce a frozen confection. The frozen confection was found to have desirable texture characteristics.

EXAMPLE 7

Cold water (129 pounds), alpha-amylase enzyme (3.5 grams), and approximately 50 pounds of partially milled oats (commonly referred to as "quick" oats) were combined in a jacketed stirred vessel to form a slurry. The slurry was heated to a temperature of approximately 71° C. over a period of about two hours. The slurry was then held at this temperature for one hour and then cooled to 66° C. to convert the slurry into an intermediate syrup. Glucoamylase enzyme (50 milliliters) was added to the intermediate syrup. The intermediate syrup was further cooled to approximately 60° C. and maintained at this temperature for one hour to convert the intermediate syrup into a syrup. The syrup, which had a very thick consistency, was diluted with water and filtered on a juice extraction machine to separate insoluble fiber from the syrup. The filtered syrup was flavored and frozen in a soft-serve machine to form a frozen confection. The frozen confection was found to have a very smooth texture and relatively low sweetness.

EXAMPLE 8

The characteristics of a non-dairy frozen confection of the present invention were studied using a commercially available oat flour obtained from Quaker Oats Company (Chicago, Ill.) known as Whole Oat #36.

A starch mixture was prepared by dispersing approximately 272 kilograms of oat flour in approximately 643 liters of cold, filtered potable water containing approximately 300 milliliters of bacterial alpha-amylase. The bacterial alpha-amylase was obtained from Genencor International (Rochester, N.Y.) under the designation DEXLO-S.

The starch mixture was prepared in hemispherical kettle with a propeller agitator. Agitation was continued without heating until the mixture was smooth and relatively free of clumps. The starch mixture was then transferred to a second hemispherical kettle having swept surface agitation.

The starch mixture was heated with indirect steam to a temperature of approximately 77° C. The slurry was then transferred to a 1000 liter holding tank and allowed to rest quiescently at an approximately constant temperature for about 30 minutes while liquefaction of the starch proceeded.

Next, the liquefied slurry was filtered by passing the slurry through a 40 inch single deck vibratory sifter fitted with a 120 mesh screen. The filtered intermediate syrup was collected in a chilled vessel. The unconverted fraction of the slurry that did not pass through the screen was discarded.

Test batches were prepared from the intermediate syrup by dispensing approximately 735 grams of the intermediate into glass containers. The containers were placed in a water bath and the cooled to approximately 60° C. Approximately 0.25 grams of glucoamylase enzyme OPTIDEX 300, which was obtained from Genencor International (Rochester, N.Y.) as added to each container. Each of the batches was stirred by hand using a spatula.

Two grams of immobilized glucose isomerase enzyme (KETOMAX® GI-101) were added to the first container. Ten grams of immobilized glucose isomerase enzyme were added to the second container.

The three containers were held in a water bath at a temperature of between about 60° C. and 63° C. for three hours with intermittent hand stirring. Small samples were withdrawn from each container after three hours.

Next, the samples were placed in plastic pouches and boiled for approximately 15 minutes to halt any enzyme activity. The samples were frozen and the sugar content of the samples was analyzed. The samples were diluted to 2 percent total solids, filtered through a 0.45 micron syringe filter, and analyzed by high pressure liquid chromatography.

The results of the analyses showing the relative amounts of fructose, glucose and disaccharide are reported in Table 3.

The designation "n/d" indicates that the sample was tested for this characteristic but was not detected.

TABLE 3

| Sample | Immobilized Glucose Isomerase Treatment | Ratio Percent Fructose | Ratio Percent Glucose | Ratio Percent Disaccharide |
|---|---|---|---|---|
| 1 | none | n/d | 86.91 | 13.09 |
| 2 | 2.0 grams | 2.27 | 84.39 | 13.34 |
| 3 | 10.0 grams | 9.96 | 75.98 | 14.06 |

The results indicate that a significant amount of glucose was converted to fructose by the action of the immobilized glucose isomerase enzyme. The results also indicate that the fructose level was related to the level of immobilized glucose isomerase enzyme.

EXAMPLE 9

The characteristics of a non-dairy frozen confection of the present invention were studied by forming a starch mixture by dispersing approximately 272 kilograms of oat flour in approximately 662 liters of cold, filtered potable water that also contained about 300 milliliters of bacterial alpha-amylase. The bacterial alpha-amylase was obtained from Genencor International (Rochester, N.Y.) under the designation DEXLO-S.

The starch mixture was prepared in a hemispherical kettle with a propeller agitator. Agitation was continued without heating until the mixture was smooth and relatively free of lumps. The starch mixture was then transferred to a second hemispherical kettle with swept surface agitation. Next, the starch mixture was heated to a temperature of approximately 77° C. using indirect steam. Once reaching this temperature, the slurry was transferred to a 1000 liter holding tank where the temperature remained relatively constant for a period of about 30 minutes while liquefaction occurred.

The liquefied slurry was filtered by passing through a 40 inch single deck vibratory sifter fitted with a 120 mesh screen. The filtered intermediate syrup was collected in a chill vessel. An unconverted fraction of the slurry, having a volume of about 180 liters, that did not pass through the screen was discarded.

A test batch of approximately 95 liters was drawn from the intermediate syrup, placed in an unmixed container, and then cooled to approximately 65° C. using a water bath. Approximately 38 milliliters of glucoamylase enzyme (SPEZYME GA300) was then stirred into the test batch. The test batch was intermittently stirred over a period of about 35 minutes.

The remaining 550 liters of intermediate syrup were cooled to about 65° C. and treated with about 214 milliliters of glucoamylase enzyme (SPEZYME GA300). This sample is subsequently referred to as the control batch. The control batch was held at a temperature of between about 55° C. and 60° C. for about 4 hours with intermittent gentle agitation while liquefaction of the starch proceeded.

Approximately 900 milliliters of immobilized glucose isomerase enzyme (KETOMAX® GI-101) were added to the test batch and the test batch was maintained at a temperature of between about 55° C. and 60° C. for approximately 3.5 hours while liquefaction and glucose isomerization of the starch proceeded. During this holding period, the test batch was frequently stirred by hand.

After the holding period, the test batch was transferred to a 24 inch diameter vibratory sifter that was fitted with a 120 mesh screen. Passing the test batch through the screen caused the immobilized glucose isomerase enzyme to be separated from the remainder of the test batch.

Samples were collected from the test batch and the control These samples were placed in a boiling water bath for approximately 15 minutes to inactivate the enzymes. The samples were each analyzed for sugar content by high pressure liquid chromatography. The results of the analyses showing the relative amounts of fructose, glucose and disaccharide are reported in Table 4.

TABLE 4

| Sample | Immobilized Glucose Isomerase Treatment | Ratio Percent Fructose | Ratio Percent Glucose | Ratio Percent Disaccharide |
| --- | --- | --- | --- | --- |
| Control Batch | none | n/d | 87.8 | 12.2 |
| Test Batch | 0.95% (vol.) | 11.8 | 75.2 | 13.0 |

The results indicate that a significant amount of glucose was converted to fructose by the action of the immobilized glucose isomerase enzyme.

Samples of the test batch and the control batch were also subjectively evaluated for sweetness. The test batch was found to be significantly sweeter than the control batch.

Although the present invention has been described with reference to preferred embodiments, workers skilled in the art will recognize that changes may be made in form and detail without departing from the spirit and scope of the invention.

What is claimed is:

1. A process for forming a syrup product that is suitable for use in a food product, the syrup product exhibiting selected sweetness, texture, and mouthfeel characteristics while being devoid of exogenous sweeteners, stabilizers, emulsifiers, and proteins, the process consisting of the steps of:

preparing a base formulation having a major amount of an oat material or waxy barley hybrid;

milling the oat material or waxy barley hybrid flour to a fine granulation so that less than 10 percent of the oat material or waxy barley hybrid flour is retained on a 200 U.S mesh screen;

blending the base formulation and water to form a slurry;

mixing alpha-amylase enzymes into the slurry;

heating the slurry to a target temperature of approximately 75° C.;

maintaining the slurry at the target temperature for approximately 1 hour to convert the slurry into an intermediate syrup;

mixing glucoamylase enzymes into the intermediate syrup; and maintaining the intermediate syrup at a saccharification temperature until the intermediate syrup is converted into the syrup product.

2. The process of claim 1, wherein the oat material is whole oat flour, low bran oat flour, patent oat flour, partially milled oats, oatmeal, or combinations thereof.

3. The process of claim 1, wherein the alpha-amylase enzymes are alpha-1,4-glucan, 4-glucanohydrolase.

4. A process for forming a syrup product that is suitable for use in a food product, the syrup product exhibiting selected sweetness, texture, and mouthfeel characteristics while being devoid of exogenous sweeteners, stabilizers, emulsifiers, and proteins, the process consisting of the steps of:

preparing a base formulation having a major amount of whole oat flour, low bran oat flour, patent oat flour, rolled oats, partially milled oats, oatmeal, waxy barley hybrid flour or combinations thereof;

milling the base formulation to a fine granulation so that less dan 10 percent of the base formulation is retained on a 200 U.S. mesh screen;

blending the base formulation and water to form a slurry;

mixing alpha-amylase enzymes into the slurry;

heating the slurry to a target temperature of less than approximately 80° C.;

maintaining the slurry at the target temperature to convert the slurry into an intermediate syrup;

mixing glucoamylase enzymes into the intermediate syrup; and maintaining the intermediate syrup at a saccharification temperature until the intermediate syrup is converted into the syrup product.

5. The process of claim 4, wherein the alpha-amylase enzymes are alpha-1,4-glucan, 4-glucanohydrolase.

* * * * *

UNITED STATES PATENT AND TRADEMARK OFFICE
CERTIFICATE OF CORRECTION

PATENT NO.   : 6,395,314 B1
DATED        : May 28, 2002
INVENTOR(S)  : Paul J. Whalen et al.

Page 1 of 1

It is certified that error appears in the above-identified patent and that said Letters Patent is hereby corrected as shown below:

<u>Title page,</u>
Item [75], Inventors, change to read -- Paul J. Whalen, Elk River, MN; Donald L. Maxwell, Plymouth, MN --.

Signed and Sealed this

Fourteenth Day of June, 2005

JON W. DUDAS
*Director of the United States Patent and Trademark Office*